(12) United States Patent
Bozzano et al.

(10) Patent No.: US 6,740,789 B1
(45) Date of Patent: May 25, 2004

(54) ALKYLAROMATIC PROCESS WITH CATALYST REGENERATION

(75) Inventors: Andrea G. Bozzano, Des Plaines, IL (US); Kurt A. Detrick, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/146,349

(22) Filed: May 14, 2002

(51) Int. Cl.[7] .............................................. C07C 2/66
(52) U.S. Cl. ......................................... 585/323; 585/449
(58) Field of Search ................................ 585/449, 323

(56) References Cited

U.S. PATENT DOCUMENTS

| | | | |
|---|---|---|---|
| 4,072,729 A | * 2/1978 | Stine et al. ................. | 585/447 |
| 5,276,231 A | 1/1994 | Kocal et al. ................. | 585/323 |
| 5,334,793 A | 8/1994 | Kocal ........................... | 585/323 |
| 6,069,285 A | 5/2000 | Fritsch et al. ............... | 585/449 |
| 6,169,219 B1 | 1/2001 | Kojima et al. .............. | 585/449 |

* cited by examiner

*Primary Examiner*—Thuan D Dang
(74) *Attorney, Agent, or Firm*—John G. Tolomei; James C. Paschall; Michael A. Moore

(57) ABSTRACT

A process for producing a product aromatic compound is disclosed which uses an on-stream alkylation reactor and an off-stream alkylation reactor, and in which at least a portion of the feed aromatic compound in the effluent stream of off-stream alkylation reactor undergoing regeneration is passed to the on-stream alkylation reactor. An embodiment of this process that uses on-stream and off-stream aromatic byproducts removal zones is also disclosed.

11 Claims, 1 Drawing Sheet

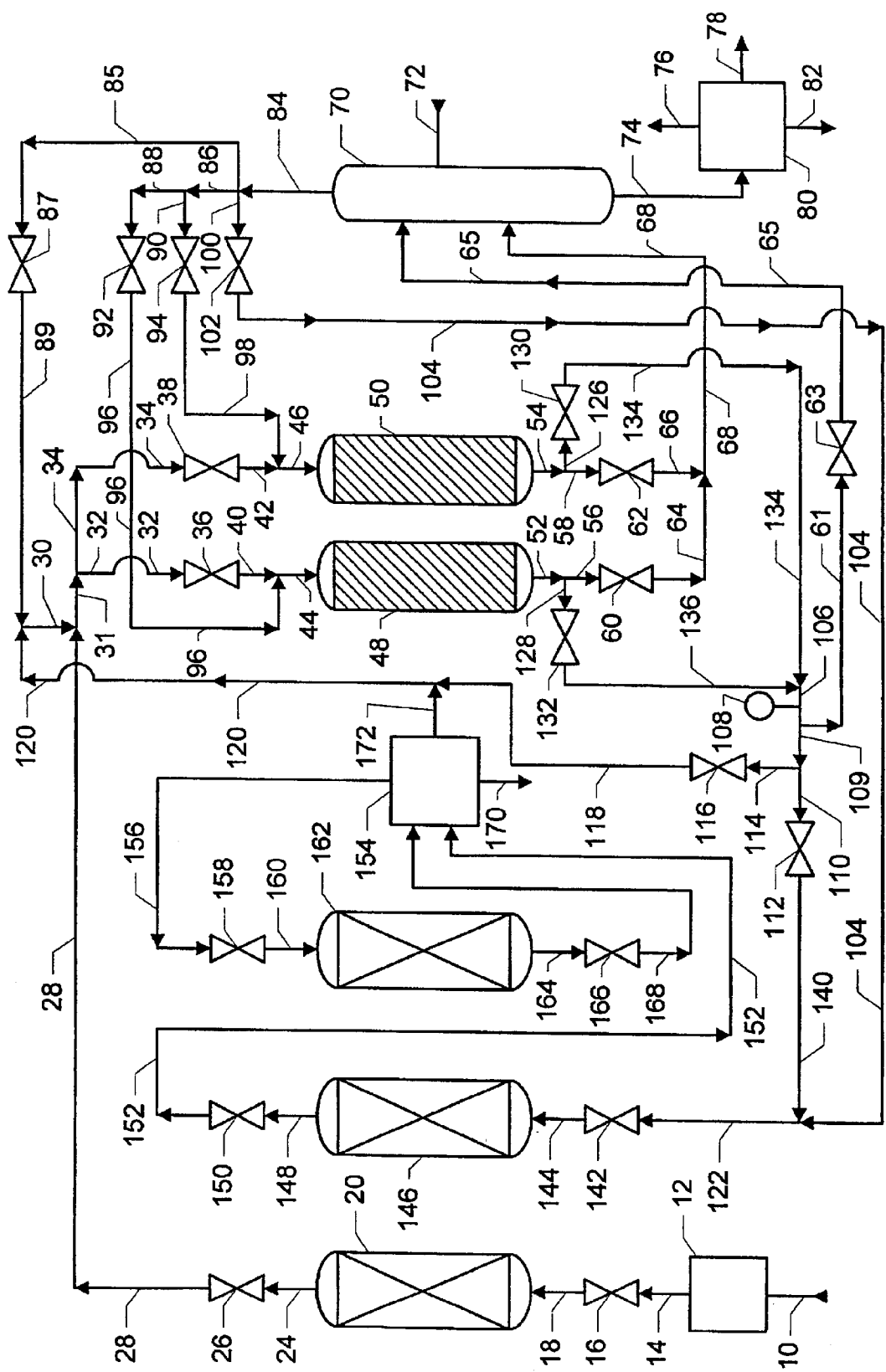

ALKYLAROMATIC PROCESS WITH CATALYST REGENERATION

FIELD OF THE INVENTION

The invention relates to the alkylation of aromatic compounds with olefins using solid catalyst

BACKGROUND OF THE INVENTION

About thirty years ago it became apparent that household laundry detergents made of heavily branched alkylbenzene sulfonates were gradually polluting rivers and lakes. Solution of the problem led to the manufacture of detergents made of linear alkylbenzene sulfonates (LABS) and later modified linear alkylbenzene sulfonates (MLABS), both of which were found to biodegrade more rapidly than the heavily branched variety. Today, detergents made using LABS and MLABS are known.

LABS are manufactured from linear alkylbenzenes (LAB), and MLABS can be made from modified linear alkylbenzenes (MLAB). The petrochemical industry produces LAB by dehydrogenating linear paraffins to linear olefins and then alkylating benzene with the linear olefins in the presence of HF. This is the industry's standard process.

Over the last decade, environmental concerns over HF have increased, leading to a search for substitute processes employing catalysts other than HF that are equivalent or superior to the standard process. Solid alkylation catalysis to produce LAB, for example, is the subject of vigorous, ongoing research. Solid alkylation catalysts can also be used to produce MLAB and are also being researched vigorously. It is known that MLAB may be made by dehydrogenating slightly branched paraffins to slightly branched olefins and then alkylating benzene with the slightly branched olefins in the presence of a solid catalyst. See, for example, U.S. Pat. Nos. 6,111,158 B1 and 6,187,981 B1, which are incorporated herein by reference.

As desirable as solid catalyst may be as an alternative to liquid HF, it is commonly the case that these catalysts deactivate with use. All alkylation catalysts, including HF and substitute catalysts for HF, lose some portion of their activity with continued use. However, the solid catalysts used to date in aromatic alkylation tend to deactivate rather quickly. Solid catalysts used for alkylation of -aromatic compounds by olefins, especially those in the 6 to 22 carbon atom range, usually are deactivated by gum-type materials that accumulate on the surface of the catalyst and block reaction sites. These materials include byproducts, such as aromatic (including polynuclear) hydrocarbons in the 10 to 22 carbon atom range, that are formed in the dehydrogenation of $C_6$ to $C_{22}$ paraffins. These materials also include undesired alkylation byproducts of higher molecular weight than the desired monoalkyl benzenes, e.g., di- and tri-alkyl benzenes, as well as olefin holigomers and other olefinic compounds.

An alkylation process using a solid alkylation catalyst typically includes means for periodically taking the catalyst out of service and regenerating it by removing these deactivating materials from the catalyst. For a solid alkylation catalyst, the catalyst life is measured in terms of time in service at constant conversion between regenerations. The longer the time between regenerations, the more desirable the catalyst and the process. Thus, it is clear that solid catalyst can be best used in the continuous alkylation of aromatics only where effective and inexpensive means of catalyst regeneration are available. Fortunately it has been observed that the deactivating materials can be readily desorbed from the catalyst by washing the catalyst with the aromatic reactant (e.g., benzene). Thus, catalyst reactivation, or catalyst regeneration as the term is more commonly employed, is conveniently effected by flushing the catalyst with an aromatic such as benzene to remove the accumulated deactivating materials from the catalyst surface, generally with restoration of 100% of catalyst activity.

A typical prior art means for regenerating the solid catalyst in an aromatic alkylation process is described in U.S. Pat. No. 6,069,285. The effluent of an alkylation reactor undergoing regeneration combines with the effluent of an on-stream alkylation reactor, and the combined effluent passes to a section of the process for recovering benzene, the alkylated benzene product, and other streams. In U.S. Pat. No. 6,069,285, this section comprises a benzene rectifier, a benzene fractionation column, and other product recovery facilities. Part of the benzene recovered from this section is recycled to the off-stream alkylation reactor to regenerate the deactivated catalyst. Another prior art process passes the effluent of the reactor undergoing regeneration to a separation zone to reject color bodies and to recover benzene that passes to the benzene fractionation column of this section.

Besides regeneration, another means for maintaining high catalyst activity is to prevent the previously mentioned aromatic byproducts formed in the dehydrogenation of paraffins from ever entering the alkylation reactors. These aromatic byproducts are believed to include, for example, alkylated benzenes, naphthalenes, other polynuclear aromatics, alkylated polynuclear hydrocarbons in the $C_{10}$–$C_{15}$ range, indanes, and tetralins, that is, they are aromatics of the same carbon number as the paraffin being dehydrogenated and may be, viewed as aromatized normal paraffins. They are typically removed using an aromatics removal zone, such as those described in U.S. Pat. Nos. 5,276,231; 5,334,793; and 6,069,285, the contents of which are incorporated herein by reference. Fixed bed sorptive separation zones that use a particulate sorbent, such as a molecular sieve (e.g., 13 X zeolite (sodium zeolite X)), are the most common aromatics removal zones.

In a typical fixed bed system, the sorbent is installed in two or more vessels in a parallel flow arrangement, so that when the sorbent bed in one vessel is spent by the accumulation of the aromatic byproducts thereon, the spent vessel is bypassed while continuing uninterrupted operation through another vessel. A purge stream comprising a purge component, such as $C_5$ or $C_6$ paraffin (e.g., normal pentane), is passed through the spent sorbent bed in the bypassed vessel in order to purge or displace unsorbed components of the stream containing the aromatic byproducts from the void volume between particles of sorbent. After purging, a regenerant or desorbent stream comprising a desorbent component such as $C_6$ or $C_7$ aromatic (e.g., benzene), is passed through the sorbent bed in the bypassed vessel in order to desorb aromatic byproducts from the sorbent. Following regeneration, the sorbent bed in the bypassed vessel is again available for use in sorbing aromatic byproducts.

Thus, a sorptive separation zone for removing the aromatic, byproducts typically produces three effluents, which approximately correspond to each of the three steps in the cycle of sorption, purge, and desorption. The composition of each of the three effluents can change during the course of each step. The first effluent, the sorption effluent, contains unsorbed components (i.e., paraffins and olefins) of the stream from which the aromatic byproducts are removed, and also typically contains the desorbent component With its decreased amount of aromatic byproducts relative to the stream that is passed to the sorptive separation zone, this effluent is used farther along in the process to produce alkylaromatics. For example, if the stream that passes to the sorptive separation zone is the dehydrogenation zone effluent, the sorption effluent contains monoolefins and paraffins and thus passes directly to the alkylation zone.

The second effluent, the purging effluent, contains the purge component, unsorbed components of the stream from which the aromatic byproducts were sorbed, and often the desorbent component. The third effluent is the desorption effluent, which contains the desorbent component, the aromatic byproducts, and the purge component The purging and desorption effluents typically are separated in two distillation columns. The desorption effluent passes to one column, which produces an overhead stream containing the desorbent and purge components and a bottom stream containing the aromatic byproducts which is rejected from the process. The overhead stream of the first column and the purging effluent pass to a second column, which separates the entering hydrocarbons into an overhead stream containing the purge component and a bottom stream containing the desorbent component and unsorbed components of the stream from which the aromatic byproducts are removed. The overhead stream of the second column is used as the purge stream. The bottom stream of the second column is used in the process to produce alkylaromatics. In the example described above where the stream that passes to the sorptive separation zone is the dehydrogenation zone effluent, the bottom stream of the second column contains benzene, monoolefins, and paraffins and flows directly to the alkylation zone. Some of the benzene in this bottom stream passes through the alkylation reactor unreacted, and is recovered in the previously mentioned section for separating the alkylation reactor effluent.

Unfortunately, the prior art uses benzene inefficiently. Separating, recovering, and recycling benzene for the on-stream alkylation reactor is a huge cost by itself. But the prior art requires much more than just that amount of benzene, because of the benzene for catalyst regeneration and/or sorbent desorption. The rewards of large reductions in capital investment and operating expenses are the incentive to developing new ways to use benzene more efficiently in, aromatic alkylation processes.

SUMMARY OF THE INVENTION

This invention is a solid catalyst alkylation process that makes multiple uses of feed aromatic that is used to regenerate the catalyst. In one embodiment of this invention, feed aromatic in the effluent of an off-stream reactor that is undergoing regeneration passes without a separation step to an on-stream alkylation reactor. Thus, feed aromatic from regeneration is re-used for alkylation. In a second embodiment, feed aromatic in the effluent of an off-stream reactor passes without an intermediate separation to a sorbent bed that is undergoing desorption. In this way, feed aromatic from regeneration is re-used for desorption. In a variation of this second embodiment, some of the feed aromatic in the effluent of the sorbent bed that is undergoing desorption passes to an, on-stream reactor, so that feed aromatic in the sorbent bed effluent is used for a total of three times before passing to the product recovery section. In this variation of the second embodiment, preferably the effluent of the sorbent bed undergoing regeneration passes to a separation section associated with the sorbent bed, and a stream comprising the feed aromatic is recovered from the separation section and passes to the on-stream reactor. All of these embodiments save capital investment and operating expenses compared to the prior art processes, since unnecessary separation, recovery, and recycling of benzene are eliminated.

A broad objective of this invention is to produce alkylated aromatics. Another objective is to make alkylated aromatics using a solid alkylation catalyst. A Third objective is to produce alkylated benzenes in a process that uses benzene more efficiently or for more uses than the prior art processes. A fourth objective is to reduce contamination by color bodies or olefinic compounds of the on-stream alkylation reactor effluent and/or the product alkylated benzenes.

Accordingly, in one embodiment this invention is a process for producing a product aromatic compound. An aromatic feed stream comprising a feed aromatic compound and an olefinic feed stream comprising the monoolefin pass to an on-stream selective alkylation reactor. In the on-stream selective alkylation reactor, the feed aromatic compound is selectively alkylated by reacting the feed aromatic compound and the monoolefin in the presence of a solid alkylation catalyst at alkylation conditions to form a product aromatic compound. The alkylation conditions are sufficient to at least partially deactivate the solid alkylation catalyst An on-stream reactor effluent stream comprising the product aromatic compound is recovered from the on-stream selective alkylation reactor. At least a portion of the on-stream reactor effluent stream passes to a product recovery section. An alkylated product stream comprising the product aromatic compound is recovered from the product recovery section. A regenerant stream comprising the feed aromatic compound passes to an off-stream selective alkylation reactor containing the solid alkylation catalyst, which is at least partially deactivated. The off-stream selective alkylation reactor operates at regeneration conditions sufficient to at least partially reactivate the solid alkylation catalyst. An off-stream reactor effluent stream comprising the feed aromatic compound is recovered from the off-stream selective alkylation reactor. At least some of the feed, aromatic compound in the off-stream reactor effluent stream passes to the on-stream selective alkylation reactor before passing to the product recovery section. The functions of the on-stream selective alkylation reactor and the off-stream selective alkylation reactor are at east intermittently shifted by operating the on-stream selective alkylation reactor to function as the off-stream selective alkylation reactor and operating the off-stream selective alkylation reactor to function as the on-stream selective alkylation reactor.

In another embodiment, this invention is a process for producing a product aromatic compound, A $C_6$–$C_{22}$ paraffinic compound is dehydrogenated in a dehydrogenation zone and a monoolefin is recovered from the dehydrogenation zone. Aromatic byproducts are formed during the dehydrogenation of the $C_6$–$C_{22}$ paraffinic compound. A dehydrogenation effluent stream comprising the paraffinic compound,, the monoolefin, and the aromatic byproducts is recovered from the dehydrogenation zone. The dehydrogenation effluent stream has a first concentration of the aromatic byproducts. Some of the aromatic byproducts are selectively removed from at least a portion of the dehydrogenation effluent stream in an on-stream aromatic byproducts removal bed. The on-stream aromatic byproducts removal bed contains a sorbent operating at sorption conditions effective to selectively sorb the aromatic byproducts. An on-stream bed effluent stream comprising the monoolefin is recovered from the on-stream aromatic byproducts removal bed. The on-stream bed effluent stream has a second concentration of the aromatic byproducts that is less than the first concentration. An olefinic feed stream comprising the monoolefin is formed from at least some of the on-stream bed effluent stream. The olefinic feed stream and an aromatic feed stream comprising a feed aromatic compound pass to an on-stream selective alkylation reactor. In the on-stream selective alkylation reactor, the feed aromatic compound is selectively alkylated by reacting the feed aromatic compound and the monoolefin in the presence of a solid alkylation catalyst at alkylation conditions to form a product aromatic compound. The alkylation conditions are sufficient to at least partially deactivate the solid alkylation: catalyst. An on-stream reactor effluent stream comprising the product aromatic compound is recovered from the on-stream selective alkylation reactor. At least a portion of the on-stream reactor effluent stream passes to a product recovery section. An alkylated product stream comprising the product aromatic compound is recovered from the product recovery section. A regenerant stream comprising the feed aromatic compound passes to an off-stream selective alkylation reactor containing the solid alkylation catalyst, which is at least partially deactivated. The off-stream selective alkylation reactor operates at regeneration conditions sufficient to at least partially reactivate the solid alkylation catalyst An off-stream reactor effluent stream comprising the feed aromatic compound is recovered from the off-stream selective alkylation reactor. Some of the off-stream reactor effluent stream passes to an off-stream aromatic byproducts removal bed which contains sorbent that contains sorbed aromatic byproducts. At desorption conditions, the aromatic byproducts are at least partially desorbed from the sorbent in the off-stream aromatic byproducts removal bed. An off-stream bed effluent stream comprising the aromatic byproducts and the feed aromatic compound is recovered from the off-stream aromatic byproducts removal bed. Some of the feed aromatic compound in the off-stream bed effluent stream passes to the on-stream selective alkylation reactor. At least intermittently the functions of the on-stream aromatic byproducts removal bed and the off-stream aromatic byproducts removal bed are shifted by operating the off-stream aromatic byproducts removal bed to function as the on-stream aromatic byproducts removal bed and operating the on-stream aromatic byproducts removal bed to function as the off-stream aromatic byproducts removal bed. The functions of the on-stream selective alkylation reactor and the off-stream selective alkylation reactor are also at least intermittently shifted by operating the on-stream selective alkylation reactor to function as the off-stream selective alkylation reactor and operating the off-stream selective alkylation reactor to function as the on-stream selective alkylation reactor.

Other objectives and embodiments of this invention are described in the detailed description.

Information Disclosure

U.S. Pat. No. 6,069,285 (Fritsch, et al.) describes an alkylation process using two alkylation reactors containing solid catalyst The effluent from the off-stream reactor combines with the effluent from the on-stream reactor, and the combined stream flows to a benzene rectifier.

U.S. Pat. Nos. 5,276,231 (Kocal et al.) and U.S. Pat. No. 5,334,793 (Kocal) describe aromatics removal zones.

U.S. Pat. No. 6,169,219 (Kojima et al.) describes measuring bromine indexes and color in the manufacture of linear alkylbenzenes and linear alkylbenzene sulfonates.

BRIEF DESCRIPTION OF THE DRAWING

The drawing shows an embodiment of the invention.

DETAILED DESCRIPTION OF THE INVENTION

Processes for the production of alkylated aromatic compounds, with and without the removal of aromatic byproducts, are well known and need not be described in detail herein. These processes are described in U.S. Pat. No. 6,069,285; 6,111,158 B1; and 6,187,981 B1. Briefly, an olefin feed stream reacts with an aromatic feed stream. The olefin feed stream contains $C_6$–$C_{22}$ monoolefins but may also contain $C_6$–$C_{22}$ paraffin and $C_6$–$C_{22}$ aromatic byproducts. The monoolefins may be linear or branched When present, the branched monoolefins may have one or two methyl or ethyl branches, but more branches and branches with more carbon numbers are possible. The aromatic feed stream contains an aromatic compound, typically benzene or alkylated derivatives of benzene. The alkylated derivatives of benzene may include toluene, xylenes, and higher methylated benzenes, ethylbenzene and higher ethylated benzenes. In the discussion that follows and for purposes of illustration, the feed aromatic compound is referred to as benzene, because it is believed that this invention will be most commonly practiced using benzene. However, this is not intended to limit the scope of this invention as set forth in the claims.

Alkylation takes place in a selective alkylation reactor in the presence of the solid alkylation catalyst. The alkylation conditions may be any conditions suitable for the catalyst, but at least partial liquid phase conditions are preferred. The solid alkylation catalyst typically has an acid function and is better known as a solid acid catalyst. Suitable solid acid catalysts include amorphous silica-alumina, crystalline aluminosilicate materials such as zeolites and molecular sieves, naturally occurring and man-made clays including pillared clays, sulfated oxides such as sulfonated zirconia, traditional Friedel-Crafts catalysts such as aluminum chloride and zinc chloride, and solid acids generally. Suitable solid alkylation catalysts are listed in U.S. Pat. No. 6,069,285, issued to T. R. Fritsch, et al., the teachings of which with respect to solid alkylation catalysts are incorporated herein by reference. Such catalysts include those described in U.S. Pat. Nos. 5,196,574 and 5,344,997, both issued to J. A. Kocal which disclose a fluorided silica-alumina catalyst, and in U.S. Pat. No. 5,302,732 issued to K. Z. Steigleder, et al., which describes an ultra-low sodium silica-alumina catalyst. In this invention, the nature of the solid alkylation catalyst is not critical to the success of this invention and is largely a matter of choice to be made by the practitioner.

In this invention, two or more selective alkylation reactors- are used, with at least one on-stream where alkylation occurs and at least one off-stream where catalyst regeneration takes place. Regeneration is effected by contacting the catalyst in the off-stream reactor with a stream comprising the feed aromatic compound (e.g., benzene).

However, after a reactor has been taken off-stream but before catalyst regeneration begins, the catalyst is typically purged to remove at least some of the unreacted monoolefins, paraffins, and alkylated benzene product from the void volume of the now off-stream reactor. Off-stream reactor purging is performed by contacting the catalyst in the off-stream reactor with a purging stream, which may comprise any suitable hydrocarbon but preferably comprises the feed aromatic compound (e.g., benzene). The source of this purging stream can be any suitable supply of benzene, for example, such as a recycle stream from the hereinafter-described product recovery section, the effluent stream of another reactor (on-stream or off-stream), or an external supply of benzene.

The off-stream reactor purging conditions are not critical to the success of this invention. The off-stream reactor purging conditions can be any conditions that are effective for at least partially purging the void volume of the alkylation catalyst Although olefins may contact the catalyst bed during off-stream reactor purging, preferably no olefins contact or pass to the catalyst during this purging. Preferably the off-stream reactor purging conditions comprise at least a partial liquid phase.

The contacting conditions for purging the catalyst in the off-stream reactor can be the same throughout the off-stream reactor purging, although some changes could be made. Although the liquid hourly space velocity (LHSV) of the benzene-containing stream may change, the contacting temperature is generally kept constant. This off-stream reactor purging can be started by simply stopping the flow of the olefinic feed stream to the on-stream reactor, thereby taking the on-stream reactor off-stream. This leaves substantially only benzene flowing to the off-stream reactor.

During off-stream reactor purging, however, the contacting temperature is preferably low enough that the previously mentioned gum-type materials that have accumulated on the catalyst are not removed. The off-stream reactor purging temperature is typically no more than 5° C. (9° F.) greater than the alkylation temperature. The temperature is usually between about 120° C. (248° F.) and about 170° C. (338° F.). In some portions of the alkylation reactor, the temperature during this step may be less than the temperature during alkylation. This is because there is less temperature rise due to less exothermic heat because less (or no) alkylation reactions are taking place.

During this off-stream reactor purging, the benzene-containing stream purges or displaces reactants and products from the void volume within the off-stream reactor. The composition of the off-stream reactor effluent will change during off-stream reactor purging. Initially, the effluent will consist mostly of benzene, unreacted monoolefin, paraffins, and alkylated benzene product. As the off-stream reactor purging proceeds and these components are displaced from the reactor, the reactor effluent will contain more benzene. As the reactor effluent contains more benzene, the Saybolt color of the reactor effluent may rise, indicating fewer color bodies in the reactor effluent. As used herein, color bodies are components of a mixture that impart color to the mixture=and Saybolt color refers to Saybolt color as determined by ASTM. D-156-00, Standard Test Method for Saybolt Color of Petroleum Products (Saybolt Chronometer Method), which is available from ASTM International, 100 Barr Harbor Drive, P.O. Box C700 West Conshohocken, Penn. USA. This off-stream reactor purging may be deemed finished when the concentration of unreacted monoolefins, paraffins, and alkylated benzene product in the reactor effluent stream drops to a relatively low level as measured by gas chromatography, for example. Alternatively, the off-stream reactor purging may be considered done when at least one reactor void volume of benzene has flowed through the off-stream reactor during purging. A third possibility is to say that this off-stream reactor purging is complete when a specified period of time has elapsed. A fourth method is feasible if the Saybolt color of the reactor effluent rises during the purging In that case, it may be said that this off-stream reactor purging is complete when the Saybolt color has risen by a specified number or has reached a specified number.

During off-stream reactor purging, at least a portion of the effluent recovered from the off-stream reactor may pass to any suitable destination, such as to another reactor (on-stream or off-stream), to an external location, or to the section of the process that is normally used for separating the on-stream reactor effluent. This section is commonly called the product recovery section and it is used to recover benzene for recycling, unreacted monoolefins and paraffins for recycling, and the alkylated benzene as product. It typically comprises a benzene distillation column a paraffin distillation column, and other distillation columns. The term portion as used herein in reference to a stream includes but is not limited to an aliquot portion of the stream, which is a portion of the stream that has the essentially the same composition as the stream.

Once off-stream reactor purging is complete, catalyst regeneration can begin. The catalyst regeneration conditions are not critical to the success of this invention. The regeneration conditions can be any conditions that are effective for at least partially reactivating the alkylation catalyst. Although olefins may contact the catalyst bed during regeneration, preferably no olefins contact or pass to the catalyst during regeneration. Preferably the regeneration conditions comprise at least a partial liquid phase.

The contacting conditions can be the same throughout the regeneration, but typically some changes in conditions are made. Commonly, the liquid hourly space velocity (LHSV) of the benzene-containing stream or the contacting temperature are changed during regeneration. Often, the LHSV of the benzene-containing stream is kept constant while the regeneration temperature is varied during the course of three steps.

The first step is a heat-up step. This instep typically begins when the temperature of the off-stream reactor is increased above the temperature during off-stream reactor purging. Raising the temperature thus can mark the end of the off-stream reactor purging, if the purging has not already been deemed finished. A flow of the regenerant (i.e., the feed aromatic compound, such as benzene) is started to the off-stream reactor at or before the start of the heat-up step.

In this step, the regeneration temperature is higher than that during off-stream reactor purging but low relative to that during the second regeneration step. The temperature during this first step starts at the temperature at the end of the off-stream reactor purging. In this step, the inlet temperature is raised by from about 50° C. (90° F.) to about 200° C. (360° F.) above the temperature of the off-stream reactor purging. The outlet temperature of the bed increases with the inlet temperature but lags behind the inlet temperature. The inlet temperature is usually raised to a temperature that depends on the particular catalyst and the nature of the catalyst deactivation. For example, for a fluorided silica-alumina catalyst, the inlet temperature is usually raised to between about 200° C. (362° F.) and about the critical temperature of the aromatic feed compound (e.g., benzene), and preferably raised to about 250° C. (482° F.). The manner and rate of inlet temperature increase is not critical to the success of this invention. Preferably, however, the inlet temperature is increased at a rate that corresponds to raising the temperature from the off-stream reactor purging temperature to the target inlet temperature of the second regeneration step during the time period for passing a reactor void volume of benzene through the off-stream reactor. The temperature may be ramped up steadily or can be increased step-wise with temperature holds. Any suitable method may be used to raise the temperature. One method is heating the benzene by indirect heat exchange and then passing it into the reactor.

As the temperature increases, the benzene-containing stream begins to remove the previously mentioned gum-type materials that accumulated on the surface of the catalyst and block reaction sites. Since some of these gum-like materials typically have some color (i.e., are color bodies), the presence of these materials in the regeneration effluent may begin to lower its Saybolt color. This step may be deemed complete when the regeneration effluent's Saybolt color begins to decline. Alternatively, this step may be considered done when the inlet temperature has been increased by about a specified fraction (e.g., one-tenth, one-third, one-half three-fourths) of the difference between the off-stream reactor purging temperature and the target inlet temperature of the second regeneration step. Since the composition of the regeneration effluent will change during this step, it is also possible to measure the concentration of the gum-like materials in the regeneration effluent stream, and to end this step when these materials have reach a specified concentration.

During this first step, at least a portion of the effluent recovered from the off-stream reactor passes to an on-stream reactor. In this way, substantially all of the components that are displaced from the off-stream reactor during this first step can be recovered in the effluent of the on-stream reactor. Of course, if the displaced benzene reacts in the on-stream reactor, what will be recovered in the on-stream reactor's effluent will include the product of any such reactions. In effect, this displaced benzene is used twice, for regenerating the catalyst in the off-stream reactor and for effecting alkylation within the on-stream reactor. Passing unreacted reactants such as benzene to the on-stream reactor gives them a second opportunity to react. But, regardless whether the displaced components react in the on-stream reactor or not, the fact that the on-stream reactor effluent passes to a benzene column and conventional facilities in the product recovery section means that the displaced components can be recovered and, if appropriate, recycled. Passing alkylated benzenes to the on-stream reactor does not adversely affect the yields of the process to a significant exdent.

If a sufficiently large amount of benzene is passed to the off-stream reactor during the first step, then that benzene itself will appear in the off-stream reactor's effluent. That benzene in the effluent will be in addition to the benzene that was originally in the void volume of the off-stream reactor prior to the start of the first step. To the extent this happens, then at least a portion of the benzene passed to the off-stream reactor during the first step will have dual use. Not only is it used for regenerating the catalyst in the off-stream reactor, but it is used, or at least present, within the on-stream reactor effecting alkylation.

The second step continues the temperature heat-up and usually includes a hold period at the elevated temperature. In this step, the inlet temperature of the off-stream alkylation reactor is raised the rest (e.g., two-thirds, one-half, or one-fourth) of the way to the target inlet temperature of the second step, which is typically from about 50° C. (90° F.) to about 200° C. (360° F.) above the temperature of the first step. They target inlet temperature is also typically from about 200° C. (392° F.) to about the critical temperature of the feed aromatic compound (e.g., benzene). As in the case of the heat-up during the first regeneration step, the manner and rate of temperature increase are not critical to the success of this invention. But preferably the rate of temperature increase during the heat-up portion of this step is substantially the same as that during the first regeneration step. Once the inlet temperature has reached its target inlet temperature, the temperature is typically held there for a specified period of time that depends on the nature of the catalyst and the extent and nature of the catalyst deactivation, typically from about 2 to about 20 hours. As the heat-up occurs, the outlet temperature of the reactor will lag behind the inlet temperature, but by the end of the hold period the outlet temperature will have generally stabilized and may have risen to a temperature close to that of the inlet temperature, depending on factors such as heat loss from the reactor. If the first regeneration step has not already been deemed finished by one of the previously-mentioned criteria, the time when the outlet temperature begins to increase in response to the raising of the inlet temperature (or a time preceding that time by some appropriate interval) can be used to mark the end of the first step.

As the temperature continues to increase and then is maintained at an elevated level, the benzene-containing stream continues to remove the gum-type materials from the surface of the catalyst. As the catalyst becomes depleted in these materials, the amount and concentration of these materials in the reactor effluent will decline. This second step can be said to be finished when the concentration of gum-like materials in the regeneration effluent stream drops to a relatively low level. Alternatively, this step can be considered complete when the time of the hold period has been reached. This step may also be deemed complete when the regeneration effluent's Saybolt color, which had fallen at the start of the second step, begins to rise. This step may also be considered done when a specified volume of benzene has flowed through the off-stream reactor during this step.

The third step is a cool-down step. The inlet regeneration temperature is reduced from the temperature at the end of the second step to the alkylation temperature. The manner and rate of temperature decrease is not critical to the success of this invention. The temperature may be ramped down steadily or dropped step-wise with temperature holds. As the temperature decreases, less of the gum-type materials are removed from the catalyst. Typically, the temperature is decreased to a temperature that is suitable for re-introducing the olefinic feed stream to the reactor. When the olefinic feed stream is re-introduced, thereby putting the off-stream reactor back on-stream, this step is deemed completed.

A preferred embodiment of this invention employs a sorptive aromatics removal zone to remove aromatic byproducts formed during dehydrogenation of paraffins to produce the olefinic feed stream. In this preferred embodiment of this invention, during the second step and preferably also the third step, at least a portion of the effluent recovered from the off-stream reactor passes to an off-streams aromatics to removal bed that is undergoing desorption. Aromatic byproducts are desorbed from the sorbent in the aromatics removal bed. Thus any benzene that was passed to the off-stream reactor during the first, second, or third steps and which enters the off-stream aromatics removal bed for desorption has two uses. First it is used to purge or regenerate the catalyst in the off-stream reactor, and then it is used to desorb aromatic byproducts from the off-stream aromatics removal bed.

The sorbent desorption conditions are not critical to the success of this invention. The desorption conditions can be any conditions that are effective for at least partially desorbing the aromatic byproducts from the sorbent. If the desorption temperature is different from the regeneration temperature, the effluent of the off-stream reactor can be heated or cooled as needed. Preferably the desorption conditions comprise at least a partial liquid phase. Suitable sorbents are disclosed in U.S. Pat. Nos. 5,276,231; 5,334,793; and 6,069,285. The nature of the sorbent is not critical to the success of this invention and is largely a matter of choice to be made by the practitioner.

The effluent of the aromatics removal bed undergoing desorption typically passes to a separation section associated with the aromatics removal zone. This section usually comprises two distillation columns or a dividing wall distillation column. The aromatic byproducts in the desorption effluent are rejected from the process in a high-boiling stream. But the benzene, olefins, and paraffins that enter this separation section (via either the effluent of an aromatics removal bed undergoing desorption or the effluent of an aromatics removal bed undergoing purging) pass to an on-stream alkylation reactor to be used in the alkylation reaction. Thus, this inversion allows for benzene that is passed to an off-stream reactor for regeneration to have as many as three uses before it passes to the product recovery section downstream of the alkylation reactors. The first use is for regenerating the catalyst in the off-stream reactor, and the second use is for desorbing aromatic byproducts from an off-stream aromatics removal bed. The third use, which follows the second use, is for effecting alkylation in an on-stream reactor.

Of course, the regeneration effluent recovered during the first, or off-stream reactor purge, step of the three-step regeneration method could be passed to an aromatics removal bed that is undergoing desorption, rather than to an on-stream alkylation reactor as described previously. But doing so could cause valuable alkylated benzene product and unreacted paraffins to be lost from the process. If these alkylated benzenes exit the aromatics removal bed during desorption, they would pass to the previously mentioned separation section associated with the aromatics removal zone. Since these alkylated benzenes are even higher boiling than the aromatic byproducts, these valuable products would be rejected from the process in the previously mentioned high-boiling stream along with the aromatic byproducts. This would hurt product yields.

When no alkylation reactor is undergoing regeneration, and particularly in the case of the previously described common three-step regeneration procedure when no alkylation reactor is undergoing either the second or third regeneration steps, there may nevertheless be a need for benzene to desorb an aromatics removal bed. Conversely, when no aromatics removal bed is being desorbed, an alkylation reactor may need to be regenerated. That is, there may be occasions when the times for desorption of an aromatics removal bed and for regeneration of an alkylation reactor do not coincide. In the, former case, benzene for desorption may be taken from any suitable source, such as the overhead of the benzene column in the separation section downstream of the alkylation reactors. In the latter case, the regeneration effluent from the off-stream reactor may be passed (or may continue to be passed) to the on-stream alkylation reactor, may be passed to the previously mentioned benzene column, or may be passed to the separation section associated with the aromatic byproducts removal zone.

Although up to this point this description has been in terms of removing aromatic byproducts from the effluent of a paraffin dehydrogenation zone, a person of ordinary skill in the art should recognize that an aromatics byproducts removal zone may be placed in one or more other locations in typical dehydrogenation-alkylation processes. One of the reasons why these additional locations are possible is that typical dehydrogenation-alkylation processes can use several optional zones or flow schemes. As for the dehydrogenation zone itself the nature of the dehydrogenation, conditions, and process flow are not critical to the success of this invention and is largely a matter of choice to be made by the practitioner, so long as the dehydrogenation zone forms some aromatic byproducts.

Having thus been formed, the aromatic byproducts may of course be selectively removed from the dehydrogenated product stream, which is recovered from the dehydrogenation zone. Where the dehydrogenated product stream passes to a stripping separation zone (e.g., a stripping column to remove light hydrocarbons), another location for the aromatic byproducts removal zone is on the stripping effluent stream that is recovered from the stripping separation zone. Third, where the overhead liquid stream of the paraffin column is recycled to the dehydrogenation zone, which is normally the case in commercial applications, the aromatic byproducts may be selectively removed from that recycle stream Fourth, where the process includes a selective monoolefin hydrogenation zone, the aromatic byproducts may be selectively removed from the selective monoolefin hydrogenation product stream, which is recovered from that zone. Fifth, where the process includes a selective diolefin hydrogenation zone, the aromatic byproducts may be selectively removed from the selective diolefin hydrogenation product stream, which is recovered from that zone. The aromatics removal zone is preferably located between the dehydrogenation zone and the selective alkylation zone because the aromatic byproducts are preferably selectively removed prior to entering the selective alkylation zone. These locations set forth above are not necessarily equivalent in terms of the required equipment, such as heaters, heat exchangers, vessels, coolers, and etc. to practice our invention. Those skilled in the art of hydrocarbon processing are able to design and provide the required equipment. But, regardless which location is selected for the bed of the aromatic byproducts removal zone in its sorption step, the bed's locations for its subsequent purging and desorption steps are as described herein.

At least a portion of the aromatic byproducts are removed so as to reduce the concentration of the aromatic byproducts in the olefinic feed stream to generally less than 2 wt-%, preferably less than about 1 wt-%, and more preferably less than 0.5 wt-% aromatic byproducts.

The drawing illustrates a preferred embodiment of the subject invention. The drawing is presented solely for purposes of illustration and is not intended to limit the scope of the invention as set forth in the claims. The drawing shows only the equipment and lines necessary for an understanding of the invention and does not show equipment such as pumps, compressors, heat exchangers, and valves which are not necessary for an understanding of the invention and which are well known to persons of ordinary skill in the art of hydrocarbon processing.

The drawing shows two alkylation reactors 48 and 50. Each reactor contains solid alkylation catalyst. Reactor 48 is on-stream and in use for alkylating benzene with olefins. Reactor 50 is off-stream for off-stream reactor purging or regeneration of the catalyst. Although not shown in the drawing, there may be one or more other on-stream reactors or other off-stream reactors, and they may be in a series- or parallel-flow arrangement. Valve 36 is open and valve 38 is closed, so that the olefin- and benzene-containing reactant stream flowing in line 31 passes through lines 32, 40, and 44 to on-stream reactor 48. Thus, there is no flow through lines 34 and 42 to off-stream reactor 50. Valve 60 is open and valve 132 is closed so that the effluent of on-stream reactor 48 passes through lines 52, 56, 64, and 68 to the benzene distillation column 70.

The drawing also shows three sorbent-containing beds, 20, 162, and 146. Each sorbent bed is performing a different function. Sorbent bed 20 is on-stream and functions to remove aromatic byproducts from a dehydrogenated product stream flowing in line 14. Sorbent bed 162 is off-stream for off-stream sorbent bed purging, and a purging stream containing n-pentane, which flows in line 156, is purging its void volume. Sorbent bed 146 is also off-stream and aromatic byproducts on its sorbent are being desorbed by a desorbent stream containing benzene which flows in line 122. Each sorbent bed is shown with an inlet valve and an inlet line,(16 and 18 for bed 20, 158 and 160 for bed 162, and 142 and 144 for bed 146, respectively), and an outlet line and an outlet valve (24 and 26 for bed 20, 164 and 166 for bed 162 and 148 and 150 for bed 146, respectively). The depicted arrangement of the inlet and outlet valves and lines of the beds permits the inlet and outlet of each bed to be closed, so that, using other additional valves and lines which are not shown but which a person of ordinary skill in the art can provide, the function of each bed can be periodically shifted to function as that of one of the other two beds in the drawing. Thus, in addition to being capable of functioning for sorption as shown in the drawing, on-stream bed 20 is also capable of functioning in the position shown in the drawing for either off-stream bed 162 (off-stream sorbent bed purging) or off-stream bed 146 (desorption). Similarly, off-stream bed 162 is also capable of functioning in the position shown for either on-stream bed 20 or off-stream bed 146, and off-stream bed 146 is also capable of functioning in the position shown for either on-stream bed 20 or off-stream bed 162. Accordingly, in normal operation, the on-stream bed 20 and off-stream beds 162 and 146 can be periodically shifted, so that on-stream bed 20 functions as off-stream bed 162, off-stream bed 162 functions as off-stream bed 146, arid off-stream bed 146 functions as on-stream bed 20.

Additional beds (not shown) may also be available for functioning in the positions shown for any of beds 20, 162, and 146. The number of beds required to operate the process depends on many factors, including the duration of the on-stream sorption, off-stream sorbent bed purging, and off-stream desorption functions; the desired extent of removal of aromatics byproducts during sorption; the desired recovery of paraffin and olefins during off-stream sorbent bed purging; and capital and operating, costs. However, a person of ordinary skill in the art can readily determine the optimum number of beds required to meet the desired objectives. In general, however, at least one sorbent bed is required, since even a single bed can function first in the position of bed 20, then in the position of bed 162, and finally in the position of bed 146, before functioning once again in the position of bed 20. More commonly, two or more beds are used, so that, as shown in the drawing, while one bed is functioning in the position of bed 20, other beds are functioning in the positions of beds 162 and 146. By shifting the functions of one or more beds, the removal of aromatic byproducts from the dehydrogenated product stream flowing in line 14 can, range from a batchwise operation with relatively long interruptions between periods of removal to an essentially continuous operation, although in practice the removal may even then be semi-continuous due to short but finite times required for shifting functions. Likewise, the off-stream sorbent bed purging and desorption functions may occur batchwise and relatively infrequently or essentially continuously.

Referring now to the dehydrogenation zone, a paraffin feed stream comprising an admixture of $C_{10}$–$C_5$, normal and branched paraffins is charged via line 10. The paraffin feed stream is usually obtained in part from the product of a paraffin adsorptive separation zone and in part from recycled paraffins recovered from the stream in line 76, although the adsorptive separation zone, the recovery of paraffins from stream 76, and the combination of these two sources of paraffins are not shown in the drawing. The paraffins enter dehydrogenation zone 12, where the paraffins are contacted with a dehydrogenation catalyst in the presence of hydrogen at conditions that effect the conversion of a significant amount of the paraffins to the corresponding olefins. Some aromatic byproducts are formed, and some diolefins may also be formed. A dehydrogenated product stream containing unreacted paraffins, monoolefins, and aromatic byproducts passes through line 14, valve 16, and line 18, and enters bed 20, which is on-stream for removal of aromatic byproducts. On-stream bed 20 contains a molecular sieve sorbent, which sorbs aromatic byproducts and removes them from the dehydrogenated product stream.

The effluent of on-stream bed 20 passes through line 24, valve 26, and line 28. It combines with a stream containing benzene, $C_{10}$–$C_{15}$ paraffins and olefins, and possibly a minor amount of n-pentane that is flowing in line 30. The combined stream flows through line 31, line 32, valve 36, and line 40. Since reactor 48 is on-stream, valve 92 is closed and no regenerant benzene is flowing through lines 88 and 96, so that the stream in line 40 is thus the inlet stream for on-stream reactor 48 flowing in line 44. The stream in line 44 may contain water but preferably the water content is minimized for most solid alkylation catalysts. Monoolefins alkylate benzene to produce alkylbenzenes in on-stream reactor 48. Reactor effluent containing alkylbenzenes, unreacted benzene, $C_{10}$–$C_{15}$ paraffins, n-pentane, and possibly water flows through line 52, line 56, valve 60, and line 64. Since reactor 50 is off-stream, valve 62 is closed so that there is no flow through line 58, valve 62, and line 66. Reactor effluent flows through line 68 to benzene column 70. Benzene column 70 produces a bottom stream in line 74 which contains alkylbenzenes and paraffins and which is sent to conventional product recovery facilities 80. Conventional product recovery facilities 80 separate the bottom stream into a paraffin-containing stream 76, a product stream containing the desired alkylbenzenes in line 78, and a stream containing heavier alkylbenzenes in line 82. Any suitable conventional facilities 80 may be used, since this invention is not limited to any particular conventional facilities 80. Typically, conventional facilities 80 comprises one distillation column, called a paraffin column, which produces the paraffin-containing stream as an overhead stream, and a second distillation column, called an alkylbenzene column, which separates the paraffin column's bottom stream into an overhead stream containing the desired alkylbenzenes and a bottom stream containing the heavier alkylbenzenes.

A makeup benzene stream enters benzene column 70 in line 72. Although Dot shown in the drawing, the overhead system of benzene column 70 typically includes an overhead condenser and an overhead receiver. The overhead system may also comprise a water boot or other conventional facilities for rejecting water from the process, since the makeup benzene stream may be wet. Benzene is recovered from the upper portion of benzene column 70. The drawing shows this benzene flowing in a single stream through line 84, with lines and valves that permit employing portions of this benzene for four different uses in the process. First, there is recycle benzene to the on-stream reactor (via line 85, valve 87, and line 89). Second, regenerant benzene is used for reactor 48 when reactor 48 is off-stream (via lines 86 and 88, valve 92, and line 96). Third, regenerant benzene is available for reactor 50 when reactor 50 is off-stream (via lines 86 and 90, valve 94, and line 98). Finally, benzene can be used for desorbing off-stream bed 146 (via line 100, valve 102, and line 104). If desired, however, benzene for each of these uses may be taken as one or more streams from one or more different locations in the upper portion of benzene column 70, such as a slip stream of overhead vapor or reflux or as a sidedraw stream.

One portion of the overhead benzene stream flows to on-stream reactor 48 by flowing via lines 84 and 85, valve 87, and line 89. Valve 87 can be used to regulate the flow rate of this portion in order to maintain a desired quantity of benzene flowing to on-stream reactor 48. This portion combines with, a stream containing benzene, $C_{10}$–$C_{15}$ paraffins and olefins, and possibly a minor amount of n-pentane that is flowing in line 120 to form the stream flowing in line 30. As described previously, the stream in line 30 combines with the stream in line 28 to form the stream in line 31, which flows through line 32, valve 36, line 40, and line 44, and enters on-stream reactor 48.

When off-stream reactor 50 is undergoing regeneration using benzene as regenerant, another portion of the overhead stream in line 84 passes to reactor 50. This portion flows through line 84, line 86, line 90, valve 94, and line 98. Since reactor 50 is off-stream, valve 38 is closed and there is no, flow through lines 34 and 42. Consequently, the portion flowing in line 98 flows through line 46 and enters reactor 50. This portion washes and/or reacts away heavy byproducts from the alkylation catalyst that cause the catalyst to deactivate. Thus, the effluent from off-stream reactor 50 contains benzene as well as these byproducts, which can include polynuclear hydrocarbons, polyalkylated aromatics, and olefin oligomers. While reactor 50 is off-stream, valve 130 is open, so that the effluent flows through line 54, line 126, valve 130, and line 134. There is no flow through lines 128 and 136 when reactor 48 is on-stream since valve 132 is closed then, and thus the stream in line 134 passes into line 106. Line 106 with its sample connection 108 thus carries effluent from either or any off-stream reactor undergoing regeneration. When the flow of effluent in line 106 exceeds the desired flow for passing to one and/or both of lines 110 and 114, then valve 63 can be opened and some of the effluent flowing in line 106 can flow to benzene column 70 through line 61, valve 63, and line 65. When valve 63 is closed, regeneration effluent does not flow into line 61 but instead flows through line 109 to the junction with lines 110 and 114.

Although either or both of valves 112 and. 116 may be open when a reactor such as 50 is off-stream being regenerated, preferably at any time during the regeneration only one of valves 112 and 116 is open and the other is closed. More preferably and specifically for the previously described three-step regeneration method, when off-stream reactor 50 is undergoing the first regeneration heat-up step, the effluent of the off-stream reactor 50 can pass to the on-stream reactor 48. To accomplish this, valve 116 is opened and valve 112 is closed. Thus, the effluent of off-stream reactor 50 flows through line 54, line 126, valve 130, line 134, line 106, line 109, line 114, valve 116, and line 118. After flowing through line 118 the effluent combines with a stream flowing in line 172 which contains benzene, $C_{10}$–$C_{15}$ paraffins and olefins, and possibly a minor amount of n-pentane to form the stream flowing in line 120. As previously described, the stream in line 120 combines with the stream in line 89 to form the stream in line 30. Thus, at least a portion of the benzene in the effluent of the off-stream reactor 50 undergoing the first step of regeneration passes to the on-stream reactor 48.

When the first step of regeneration is completed, as determined by analyses of the effluent at sample connection 108, the effluent of the off-stream reactor 50 can pass to the off-stream sorbent bed 146 undergoing desorption. To do this, valve 116 is closed and valve 112 is opened. During the second. (hold) and third (cool-down) steps of the three-step regeneration method, the effluent of off-stream reactor 50, after discharging from line 109, flows through line 110, valve 112, and line 140. If the flow of regeneration effluent through line 140 is sufficient for desorption of off-stream sorbent bed 146, then there is no need to supplement the flow in line 140 with additional benzene from benzene column 70. In that case, valve 102 is closed, and there is no flow of benzene through line 100, valve 102, and line 104. Accordingly, the regeneration effluent in line 140 flows through line 122, valve 142, and line 144, and into off-stream sorbent bed 146.

Usually, when an alkylation reactor, such as 50, is undergoing regeneration and its effluent is flowing to a sorbent bed such as 146 that is undergoing desorption, the effluent of the alkylation reactor undergoing regeneration will provide a sufficient flow rate of benzene to desorb the off-stream sorbent bed. If, however no alkylation reactor is being regenerated, or if the rate of benzene flow from the alkylation reactor being regenerated to the sorbent bed undergoing desorption is insufficient to desorb the sorbent bed, then benzene must be supplied to the sorbent bed undergoing desorption from a source other than the effluent of any alkylation reactor undergoing regeneration. In these circumstances, benzene is made available by opening valve 102 so that benzene flows through line 100, valve 102, and line 104. From there, the benzene combines with the flow from line 140, if any, and flows to the off-stream bed 146 via lines 122 and 144.

The effluent of sorbent bed 146 undergoing desorption flows through line 148, valve 150, and line 152 to separation zone 154. The effluent of bed, 162 which is undergoing off-stream sorbent bed purging flows through line 164, valve 166, and line 168, and also enters separation zone 154. Separation zone 154 separates the entering streams into a low-boiling stream in line 156 that contains the purge compound (e.g. n-pentane), a high-boiling stream in line 170 that contains aromatic byproducts desorbed from the sorbent bed 146, and an intermediate-boiling stream in-line 172 that contains benzene and paraffins and olefins that have been purged from sorbent bed 162. The low-boiling stream in line 156 is recycled to sorbent bed 162, the high boiling stream in line 170 is rejected from the process, and the intermediate boiling stream combines with the stream flowing in line 118, if any, so that the paraffins and olefins in line 172 ultimately pass to the on-stream reactor 48. Thus, at least a portion of the benzene in the effluent of the off-stream reactor 50 undergoing the second and/or third steps of regeneration also passes to the on-stream reactor 48, albeit by way of the off-stream sorbent bed 146 and separation zone 154.

Separation zone 154 may be any arrangement of distillation columns known to a person of ordinary skill in the art suitable for performing this separation, and this invention is not limited to any particular separation zone 154. Typically, separation zone 154 comprises two distillation columns in series. The stream flowing in line 152 passes to a first column, from which the stream flowing in line 170 is rejected as a bottom stream. The first column also produces an overhead stream, which passes to a second column along with the stream flowing in line 168. The stream flowing through line 156 is recovered from the overhead of the second column, and the stream flowing in line 172 is recovered as a bottom stream from the second column.

In addition to rejecting aromatic byproducts from the process, separation zone 154 can also reject from the process the gum-like materials including color bodies and/or olefinic compounds removed from the off-stream reactor 50, when the effluent of off-stream reactor 50 passes to off-stream sorbent bed 146. It has been observed that at typical desorption conditions the gum-like materials are not sorbed on the sorbent in off-stream sorbent bed 146. These relatively high-boiling compounds can pass to separation zone 154, where they can be rejected in the high-boiling stream in line 170 or in another high-boiling stream. Another method of rejecting these gum-like materials from the process, without passing the effluent of the off-stream reactor 50 to either the off-stream sorbent bed 146 or to the conventional product recovery facilities 80, is to pass the effluent of off-stream reactor 50 to separation zone 154. This is another more-direct way of rejecting these gum-like materials in a high-boiling stream from separation zone 154. Thus, this invention can help prevent these gum-like materials from passing to benzene column 70 and product recovery facilities 80.

By keeping these gum-like materials from entering benzene column 70 and product recovery facilities 80, this invention can improve the bromine index of the alkylated product. Accordingly, in another embodiment, this invention is a process for controlling the bromine index of the alkylated product at a target specification or within a specified range by regulating the flow of off-stream reactor 50 effluent to off-stream stream sorbent bed 146. Production of high-quality alkylated product, having a bromine index as measured by UOP Method 304-90 of less than 20, preferably of less than 10, can be controlled. Although low-quality product is not normally desired, this invention can also be used to control the production of alkylated product having a bromine index as measured by UOP Method 304-90 of greater than 20, of up to 100, or of even more than 100. Information on UOP Method 304-90, "Bromine Number and Bromine Index of Hydrocarbons by Potentiometric Titration," is available from ASTM International. It should be pointed out that there are at least three other standard test methods for bromine index, including ASTM D 1492, "Bromine Index of Aromatic Hydrocarbons by Coulometric Titration;" ASTM. D 5776, "Bromine Index of Aromatic Hydrocarbons by Electrometric Titration;" and ASTM D 2710, "Bromine Index of Petroleum Hydrocarbons by Electrometric Titration." Information on these ASTM methods is also available from ASTM International. UOP Method 304-90 is not equivalent to each of these or other methods of measuring bromine index, and therefore it is to be understood that the above mentioned numerical values of bromine index are as measured by UOP Method 304-90 only.

It is believed that the alkylated product of this invention has a Saybolt color of more than +25, preferably of +29 or more, and more preferably +30 or more. Also, it is well known that improving the bromine index of the alkylated product leads to an improvement in the Klett color index of sulfonated alkylbenzenes produced therefrom.

Although in the preceding description alkylation reactor 48 is on-stream and alkylation reactor 50 is off-stream, the functions of the two reactors may be switched. When alkylation reactor 48 is off-stream and alkylation reactor 50 is on-stream, the effluent of reactor 48 may be passed to reactor 50 during certain periods of the regeneration of reactor 48, as previously described for the case of alkylation reactor 48 being on-stream and alkylation reactor 50 being off-stream. Thus, during regeneration of reactor 48, when valve 132 is open and valve 60 is closed, the effluent of reactor 48 may pass through line 128, valve 132, line 136, line 106, and line 109. With valve 112 closed and valve 116 open, the effluent flows through line 114, valve 116, and line 118. From line 118, the effluent combines with the stream flowing in line 172 and the combined stream in line 120, including benzene from the off-stream reactor 48 effluent, ultimately flows to reactor 50 via lines 30, 31, 34, 42, and 46. A sample of the effluent of reactor 48 may be taken for analysis at sample connection 108. When the regeneration effluent of reactor 48 is passed to off-stream sorbent bed 146, valve 112 is opened and valve 116 is closed, so that the effluent passes through line 1110, valve 112, line 140, line 122, valve 142, and line 144 to sorbent bed 146. As described previously, the effluent of sorbent bed 146 flows to separation zone 154, and benzene recovered in line 172 enters line 120 and ultimately passes to on-stream reactor 50.

What is claimed is:

1. A process for producing a product aromatic compound, the process comprising:

a) dehydrogenating a $C_6$–$C_{22}$ paraffinic compound to form a monoolefin and producing aromatic byproducts in a dehydrogenation zone, and recovering from the dehydrogenation zone a dehydrogenation effluent stream comprising the paraffinic compound, the monoolefin, and the aromatic byproducts and having a first concentration of the aromatic byproducts;

b) selectively removing at least a portion of the aromatic byproducts from at least a portion of the dehydrogenation effluent stream in an on-stream aromatic byproducts removal bed containing a sorbent at sorption conditions effective to selectively sorb the aromatic byproducts;

c) recovering from the on-stream aromatic byproducts removal bed an on-stream bed effluent stream comprising the monoolefin, wherein the on-stream bed effluent stream has a second concentration of the aromatic byproducts that is less than the first concentration;

d) passing an aromatic feed stream comprising a feed aromatic compound and at least a portion of the on-stream bed effluent stream comprising the monoolefin to an on-stream selective alkylation reactor, selectively alkylating the feed aromatic compound by reacting the feed aromatic compound and the monoolefin in the presence of a solid alkylation catalyst in the on-stream selective alkylation reactor at alkylation conditions to form a product aromatic compound, the alkylation conditions being sufficient to at least partially deactivate the solid alkylation catalyst, and recovering from the on-stream selective alkylation reactor an on-stream reactor effluent stream comprising the product aromatic compound;

e) passing at least portion of the on-stream reactor effluent stream to a product recovery section, and recovering from the product recovery section an alkylated product stream comprising: the product aromatic compound;

f) passing a regenerant stream comprising the feed aromatic compound to an off-stream selective alkylation reactor containing the solid alkylation catalyst, wherein the solid alkylation catalyst in the off-stream selective alkylation reactor is at least partially deactivated, the off-stream selective alkylation reactor operates at regeneration conditions sufficient to at least partially reactivate the solid alkylation catalyst, and recovering an off-stream reactor effluent stream comprising the feed aromatic compound from the off-stream selective alkylation reactor;

g) at least intermittently shifting the functions of the on-stream selective alkylation reactor and the off-stream selective alkylation reactor by operating the on-stream selective alkylation reactor to function as the off-stream selective alkylation reactor and operating the off-stream selective alkylation reactor to function as the on-stream selective alkylation reactor;

h) passing at least portion of the off-stream reactor effluent stream to an off-stream aromatic byproducts removal bed containing sorbent, the sorbent in the off-stream aromatic byproducts removal bed containing sorbed aromatic byproducts to at least partially desorb the aromatic byproducts from the sorbent in the off-stream aromatic byproducts removal bed at desorption condition;

i) recovering from the off-stream aromatic byproducts removal bed an off-stream bed effluent stream comprising the feed aromatic compound;

j) passing at least a portion of the feed aromatic compound in the off-stream bed effluent stream to the on-stream selective alkylation reactor; and k) at least intermittently shifting the functions of the on-stream aromatic byproducts removal bed and the off-stream aromatic byproducts removal bed by operating the off-stream aromatic byproducts removal bed to function as the on-stream aromatic byproducts removal bed and operating the on-stream aromatic byproducts removal bed to function as the off-stream aromatic byproducts removal bed.

2. The process of claim 1 further characterized in that the aromatic byproducts are passed to the on-stream selective alkylation reactor.

3. The process of claim 1, wherein the passing of at least a portion of the feed aromatic compound in the off-stream bed effluent stream to the on-stream selective alkylation reactor comprises passing at least a portion of the off-stream bed effluent stream to a separation zone, and passing at least a portion of the return stream to the on-stream selective alkylation reactor.

4. The process of claim 3, further characterized in that the separation zone comprises a distillation column.

5. The process of claim 1, further characterized in that the regeneration conditions comprise a regeneration temperature of from about 200° C. to about the critical temperature of the feed aromatic compound.

6. The process of claim 1 further characterized in that the alkylated product stream has a bromine index of less than 20.

7. A process for producing a product aromatic compound, the process comprising:

a) dehydrogenating a $C_6$–$C_{22}$ paraffinic compound to form a monoolefin and producing aromatic byproducts in a dehydrogenation zone, and recovering from the dehydrogenation zone a dehydrogenation effluent stream comprising the monoolefin, the paraffinic compound, and the aromatic byproducts;

b) passing an aromatic feed stream comprising a feed aromatic compound and at least a portion of the dehydrogenation effluent stream comprising the monoolefin and the $C_6$–$C_{22}$ paraffinic compound to an on-stream selective alkylation reactor, selectively alkylating the feed aromatic compound by reacting the feed aromatic compound and the monoolefin in the presence of a solid alkylation catalyst in the on-stream selective alkylation reactor at alkylation conditions to from a product aromatic compound, the alkylation conditions being sufficient to at least partially deactivate the solid alkylation catalyst, and recovering from the on-stream selective alkylation reactor an on-stream reactor effluent stream comprising the product aromatic compound;

c) passing at least a portion of the on-stream reactor effluent stream to a product recovery section, and recovering from the product recovery section an alkylated product stream comprising the product aromatic compound and a paraffin recycle stream comprising the $C_6$–$C_{22}$ paraffinic compound and aromatic byproducts, wherein the paraffin recycle stream has a first concentration of aromatic byproducts;

d) selectively removing at least a portion of aromatic byproducts from at least a portion of the paraffin recycle stream in an on-stream aromatic byproducts removal bed containing a sorbent at sorption conditions effective to selectively sorb aromatic byproducts;

e) recovering an on-stream bed effluent steam comprising the $C_6$–$C_{22}$ paraffinic compound from the on-stream aromatic byproducts removal bed, wherein the on-stream bed effluent stream has a second concentration of aromatic byproducts that is less than the first concentration;

f) providing at least a portion of the $C_6$–$C_{22}$ paraffinic compound dehydrogenated in the dehydrogenation zone from at least a portion of the on-stream bed effluent stream;

g) passing a regenerant stream comprising the feed aromatic compound to an off-stream selective alkylation reactor containing the solid alkylation catalyst, wherein the solid alkylation catalyst in the off-stream selective alkylation reactor is at least partially deactivated, the off-stream selective alkylation reactor operates at regeneration conditions sufficient to at least partially reactivate the solid alkylation catalyst, and recovering an off-stream reactor effluent stream comprising the feed aromatic compound from the off-stream selective alkylation reactor;

h) at least intermittently shifting the functions of the on-stream selective alkylation reactor and the off-stream selective alkylation reactor by operating the on-stream selective alkylation reactor to function as the off-stream selective alkylation reactor and operating the off-stream selective alkylation reactor to function as the on-stream selective alkylation reactor and operating the off-stream selective alkylation reactor to function as the on-stream selective alkylation reactor;

i) passing at least a portion of the off-stream reactor effluent stream to an off-stream aromatic byproducts removal bed containing sorbent, the sorbent in the off-stream aromatic byproducts removal bed containing sorbed aromatic byproducts, to at lest partially desorb aromatic byproducts from the sorbent in the off-stream aromatic byproducts removal bed at desorption conditions;

j) recovering from the off-stream aromatic byproducts removal bed an off-stream bed effluent stream comprising aromatic byproducts and the feed aromatic compound;

k) passing at least a portion of the feed aromatic compound in the off-stream aromatic byproducts bed effluent stream to the on-stream selective alkylation reactor; and l) at least intermittently shifting the functions of the on-stream aromatic byproducts removal bed and the off-stream aromatic byproducts removal bed by operating the off-stream aromatic byproducts removal bed to function as the on-stream aromatic byproducts removal bed and operating the on-stream aromatic byproducts removal bed to function as the off-stream aromatic byproducts removal bed.

8. The process of claim 7 wherein the passing of at least a portion of the feed aromatic compound in the off-stream bed effluent stream to the on-stream selective alkylation reactor comprises passing at least a portion of the off-stream bed effluent stream to a separation zone, recovering a return stream comprising the feed aromatic compound from the separation zone, and passing at least a portion of the return stream to the on-stream selective alkylation reactor.

9. The process of claim 8 further characterized in that the separation zone comprises a distillation column.

10. The process of claim 7 further characterized in that the regeneration conditions comprise a regeneration temperature of from about 200° C. to about the critical temperature of the feed aromatic compound.

11. The process of claim 7 further characterized in that the alkylated product stream has a bromine index of less than 20.

* * * * *

UNITED STATES PATENT AND TRADEMARK OFFICE
CERTIFICATE OF CORRECTION

PATENT NO. : 6,740,789 B1
DATED : May 25, 2004
INVENTOR(S) : Bozzana et al.

It is certified that error appears in the above-identified patent and that said Letters Patent is hereby corrected as shown below:

Column 19,
Line 36, immediately following "zone," insert -- recovering a return stream comprising the feed aromatic compound from the separation zone --.

Column 20,
Line 44, delete the repeated phrase "and operating the off-stream selective alkylation reactor to function as the on-stream selective alkylation reactor".
Line 51, "lest" should be replaced with -- least --.

Signed and Sealed this

Twenty-third Day of November, 2004

JON W. DUDAS
*Director of the United States Patent and Trademark Office*